United States Patent
Sarachan et al.

(10) Patent No.: US 9,785,848 B2
(45) Date of Patent: Oct. 10, 2017

(54) AUTOMATED STAINING AND SEGMENTATION QUALITY CONTROL

(71) Applicant: GE Healthcare Bio-Sciences Corp., Piscataway, NJ (US)

(72) Inventors: Brion Daryl Sarachan, Niskayuna, NY (US); Alberto Santamaria-Pang, Niscayuna, NY (US); Yousef Al-Kofahi, Niscayuna, NY (US); Edward John Moler, Aliso Viejo, CA (US); Raghav Krishna Padmanabhan, Aliso Viejo, CA (US); Qing Li, Niskayuna, NY (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 175 days.

(21) Appl. No.: 14/701,424

(22) Filed: Apr. 30, 2015

(65) Prior Publication Data
US 2016/0321512 A1 Nov. 3, 2016

(51) Int. Cl.
G06K 9/00 (2006.01)
G06K 9/03 (2006.01)
G01N 1/30 (2006.01)
G06F 19/00 (2011.01)

(52) U.S. Cl.
CPC .............. *G06K 9/036* (2013.01); *G01N 1/30* (2013.01); *G06F 19/366* (2013.01); *G06K 9/0014* (2013.01)

(58) Field of Classification Search
None
See application file for complete search history.

(56) References Cited

U.S. PATENT DOCUMENTS

| | | | |
|---|---|---|---|
| 8,639,013 B2 | 1/2014 | Kenny | |
| 8,824,769 B2 | 9/2014 | Sarachan | |
| 2011/0091081 A1 | 4/2011 | Sarachan | |
| 2013/0287283 A1* | 10/2013 | Kamath | G09G 5/026 382/133 |

(Continued)

OTHER PUBLICATIONS

Rizk, A., Paul, G., Incardona, P., Bugarski, M., Mansouri, M., Niemann, A., . . . & Sbalzarini, I. F. (2014). Segmentation and quantification of subcellular structures in fluorescence microscopy images using Squassh. Nature protocols, 9(3), 586-596.*

(Continued)

*Primary Examiner* — Vu Le
*Assistant Examiner* — Samah Beg

(57) ABSTRACT

The disclosed subject matter relates to an automated determination the stain quality and segmentation quality of a tissue sample. By way of example, separate image data is acquired of an unstained form of a biological specimen, the biological specimen stained with a nuclei marker and the biological specimen stained with a segmentation marker. A correlation map (Cr) from the separate image data and a ridgeness map (Pr) from the image data of the biological specimen stained with a segmentation marker are each determined. A staining quality score and segmentation quality score are then determined from the correlation map (Cr) and the ridgeness map (Pr).

19 Claims, 11 Drawing Sheets
(8 of 11 Drawing Sheet(s) Filed in Color)

(56) References Cited

U.S. PATENT DOCUMENTS

2014/0314299 A1 10/2014 Santamaria-Pang
2015/0133321 A1 5/2015 Bhaumik

OTHER PUBLICATIONS

"Quantitative measurement of cancer tissue biomarkers in the lab and in the clinic", Daniel E Carvajal-Hausdorf, Kurt A Schalper, Veronique M Neumeister and David L Rimm; Laboratory Investigation (2015) 95, 385-396; doi:10.1038/labinvest.2014.157; published online Dec. 15, 2014.

* cited by examiner

AUTOMATED STAINING AND SEGMENTATION QUALITY CONTROL

BACKGROUND

The subject matter disclosed herein generally relates to analyzing the expression of biomarkers in cells that are examined in situ in their tissue of origin. More particularly, the disclosed subject matter relates to an automated determination the stain quality and segmentation quality of a tissue sample.

The expression of biomarkers in cells and tissues has been an important technique for biological and medical research relating to, for example, drug development, disease pathways, tissue pathology and clinical studies. Available biomarkers allow for the determination of a specific cell or components of a cell such as cytoplasm, membrane or nucleus based on the level of expression of a given biomarker. Historically, tissue treated with several biomarkers that each emanate different signals have been analyzed using digital imagery. However, more recently, techniques have been developed that allow for the examination of a single specimen using a greater number of biomarkers, thus providing more information and data available for analysis. Sequential multiplexing techniques involve staining a specimen using a fluorophore labeled probe to indicate the expression of one or more probe bound biomarkers, chemically bleaching the specimen and re-staining the specimen with a different probe bound biomarker. A probe bound biomarker may also be referred to as a "biomarker."

Sequential multiplexing technology used, for example, in the GE Healthcare MultiOmyx™ platform has enabled researchers to perform studies in which a large number of biomarkers (60+) can be analyzed at the cell level. Such technology allows a single tissue sample to be examined and data collected sequentially using different biomarkers.

The analysis of a typical multiplexing study may take several weeks to months depending on the sample size and number of used biomarkers. As part of the process, a large portion of the time is spent performing manual quality control (QC) steps, including, for example, tissue, staining, segmentation and normalization QC. In addition to being time consuming, manual QC may be subject to human error, including, for example, a lack of repeatability and observer-to-observer inconsistency. There is a need to reduce the overall time of a typical multiplexing study as well as improve repeatability and consistency of the QC decisions. As a result, the cost of conducting such studies can be reduced and overall efficiency increased.

BRIEF DESCRIPTION

In one embodiment, a method for determining the quality of a segmentation marker stained biological specimen is provided. The method includes acquiring separate image data of an unstained form of a biological specimen, the biological specimen stained with a nuclei marker and the biological specimen stained with a segmentation marker; determining a correlation map (Cr) from the separate image data of the unstained form of the biological specimen, the biological specimen stained with the nuclei marker and the biological specimen stained with the segmentation marker; determining a ridgeness map (Pr) from the image data of the biological specimen stained with the segmentation marker; and determining a staining quality score from the correlation map (Cr) and the ridgeness map (Pr).

In another embodiment, a system for assessing the quality of a segmentation marker stained biological specimen is provided. The system includes a memory configured to store instructions for acquiring separate image data of an unstained form of a biological specimen, the biological specimen stained with a nuclei marker and the biological specimen stained with a segmentation marker; determining a correlation map (Cr) from the separate image data of the unstained form of the biological specimen, the biological specimen stained with the nuclei marker and the biological specimen stained with the segmentation marker; determining a ridgeness map (Pr) from the image data of the biological specimen stained with the segmentation marker; and determining a staining quality score from the correlation map (Cr) and the ridgeness map (Pr). The system also includes a processor configured to execute the instructions.

In another embodiment, an imaging system for assessing the quality of a segmentation marker stained biological specimen is provided. The system includes an imager configured to acquire image data of a biological specimen; data processing circuitry configured to process the image data into processed image data; and a memory. The memory is configured to store the image data and the processed image data as well as instructions for acquiring separate image data of an unstained form of the biological specimen, the biological specimen stained with a nuclei marker and the biological specimen stained with a segmentation marker; determining a correlation map (Cr) from the separate image data of the unstained form of the biological specimen, the biological specimen stained with the nuclei marker and the biological specimen stained with the segmentation marker; determining a ridgeness map (Pr) from the image data of the biological specimen stained with the segmentation marker; and determining a staining quality score from the correlation map (Cr) and the ridgeness map (Pr); The data processing circuitry is configured to execute the instructions stored in the memory.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

Figure 1:
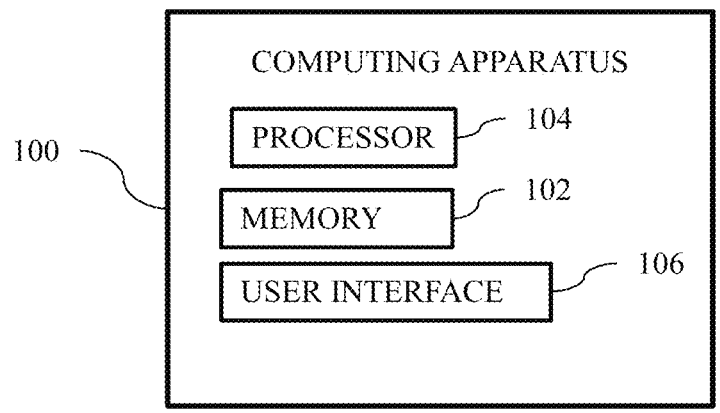
FIG. 1 illustrates a block diagram of an exemplary computing apparatus.

The patent or application file contains at least one drawing executed in color. Copies of this patent or patent application publication with color drawing(s) will be provided by the Office upon request and payment of the necessary fee.

DETAILED DESCRIPTION

The present disclosure relates to determining the quality of a specimen undergoing multiplexing biomarker analysis using, for example, the GE Healthcare MultiOmyx™ platform. In one embodiment, the disclosed embodiments may be used to determine the staining quality and segmentation quality of a specimen. For example, staining and segmentation quality scores can be obtained in the range of 0 to 10. Such scores may be used to ascertain images of good quality (high quality scores), reject images with poor quality (low quality scores) and flag images for further review (intermediate quality scores), including for example, manual review. As a result, the number of images that require manual review is reduced.

Further benefits of the embodiments of the present disclosure include the following: (1) reducing analysis time that enables faster scale-up for studies, particularly very large studies, as a result of, for example, its use in a high-throughput commercial business environment; (2) reducing errors that may degrade the quality of the analytical results; and (3) reducing human subjectivity and observer to observer variability, which improves the repeatability and reliability of the results. In addition to the quality score, the embodiments may also provide a good staining mask, which can be used to accept/reject specific regions of a specimen image, thus, reducing the loss of high quality data resulting from throwing away an entire image whose overall quality score is not acceptable, but that includes image regions with an acceptable quality score.

Embodiments of the present disclosure may be performed in situ, including, for example, in intact organ or tissue or in a representative segment of an organ or tissue. In situ analysis can include cells obtained from various sources, including an organism, an organ, tissue sample, or a cell culture. Analysis thereof may provide specimen data that is difficult to obtain should the cells be removed from their biological surroundings. Acquiring such may not be possible should the cells within the specimen be disturbed from their natural tissue milieu.

As used herein, the terms "specimen," "biological specimen,' "biological material," or "biological sample" refers to material obtained from, or located in, a biological subject, including biological tissue or fluid obtained from a subject, including, but are not limited to, body fluid (e.g., blood, blood plasma, serum, or urine), organs, tissues, biopsies, fractions, and cells isolated from, or located in, any biological system, such as mammals. Specimens, biological specimens, biological samples and/or biological materials also may include sections of a biological sample, specimens or materials including tissues (e.g., sectional portions of an organ or tissue) and may also include extracts from a biological sample, for example, an antigen from a biological fluid (e.g., blood or urine). The specimens, biological specimens, biological samples and/or biological materials may be imaged as part of a slide.

The present disclosure includes embodiments involving systems and methods for biological specimen image analysis including those that may be used to analyze images from a physical sample or previously acquired images, for example, digitally stored images. In other embodiments, the images may be acquired from a physical sample. An exemplary imaging system may include an imager that detects signals and converts the signals to data that may be processed by system processors. The imager creates image data indicative of a biological specimen in a conventional medium, such as photographic film, or in a digital medium. The imager may utilize various physical principles for creating the derived image data including, for example, a fluorescent microscope, a bright field microscope, or devices adapted for suitable imaging modalities.

The imager may operate under the control of system control circuitry that may include a wide range of circuits, including, for example, illumination sources control circuits, timing circuits, circuits for coordinating data acquisition in conjunction with sample movements, circuits for controlling the position of light sources and detectors, and so forth. In one embodiment, the system control circuitry may include one or more processor-based components including a computing apparatus, such as a general purpose or application specific computer. The system control circuitry may also include computer-readable memory elements, such as magnetic, electronic, or optical storage media, for storing programs and routines executed by the system control circuitry or by associated components of the system. The stored programs or routines may include programs or routines for performing all or part of the embodiments of the present disclosure.

Image data acquired by the imager may be processed by the imager, for a variety of purposes, including, for example, to convert the acquired data or signal to digital values, that may be provided to data acquisition circuitry. In one embodiment, the data acquisition circuitry may include one or more processor-based components including a computing apparatus, such as a general purpose or application specific computer. The data acquisition circuitry may perform a wide range of processing functions, including, for example, adjustment of digital dynamic ranges, smoothing or sharpening of data, as well as compiling of data streams and files, where desired. The processing functions may include performing all or part of the embodiments of the present disclosure.

The data acquisition circuitry may also transfer acquisition image data to data processing circuitry, where, for example, additional processing and analysis may be performed, such as substantial analyses of image data, including ordering, sharpening, smoothing, feature recognition, and so forth. The processed image data may be stored in short or long term storage devices, such as picture archiving communication systems, which may be located within or remote from the imaging system and/or reconstructed and displayed for an operator, such as at an operator workstation.

The data acquisition circuitry may also transfer acquisition image data to data processing circuitry, where additional processing and analysis may be performed. In one embodiment, the data processing circuitry may include one or more processor-based components including a computing apparatus, such as a general purpose or application specific computer. Thus, the data processing circuitry may perform substantial analyses of image data, including ordering, sharpening, smoothing, feature recognition, and so forth. The processing functions may include performing all or part of the embodiments of the present disclosure. In addition, the data processing circuitry may receive data for one or more sample sources. The processed image data may be stored in short or long term storage devices, such as picture archiving communication systems, which may be located within or remote from the imaging system and/or reconstructed and displayed for an operator, such as at an operator workstation.

The operator workstation may display reconstructed images, control the above-described operations and functions of the imaging system, utilizing, for example, an interface with the system control circuitry. The operator workstation may include one or more processor-based components including a computing apparatus, such as a general purpose or application specific computer. The computer may also include various memory and/or storage components including magnetic and optical mass storage devices and internal memory, such as RAM chips. Programs and routines for performing the embodiments of the present disclosure may be stored using such memory and/or storage components included in the operator workstation or by associated components of the system, including a computer accessible storage and/or memory accessible by network and/or communication interfaces present on the computer. The one or more processor-based components may perform all or part of the embodiments of the present disclosure. The one or more processor-based components may also comprise various input/output (I/O) interfaces (including wires, lines, or suitable wireless interfaces (including WIFI, Bluetooth or cellular telephone interfaces) and various network or communication interfaces including local and wide area intranets and storage networks as well as the Internet to allow for communication with various user interface devices, including, for example, a display, keyboard, mouse and printer. The display may include screen or other devices to provide a visual image for the imaging system and, may also include a touch screen that may operate as an input device as well. Such interfaced devices may be used for viewing and inputting configuration information and/or for operating the imaging system.

More than a single operator workstation may be provided for the imaging system. For example, an imaging scanner or station may include an operator workstation which permits regulation of the parameters involved in the image data acquisition procedure, whereas a different operator workstation may be provided for manipulating, enhancing, and viewing results and reconstructed images, such that, for example, the embodiments of the present disclosure involving, for example, image processing and segmenting described herein may be carried out remotely from the imaging system.

In at least one aspect of the disclosed embodiments, the systems and methods disclosed herein may be executed by one or more computers or processor-based components under the control of one or more programs stored on computer readable medium, such as a non-transitory computer readable medium. FIG. 1 shows a block diagram of an exemplary computing apparatus 100 that may be used to practice aspects of the disclosed embodiment. In at least one exemplary aspect, the system control circuitry, data acquisition circuitry, data processing circuitry, operator workstation and other disclosed devices, components and systems may be implemented using an instance or replica of the computing apparatus 100 or may be combined or distributed among any number of instances or replicas of computing apparatus 100.

The computing apparatus 100 may include computer readable program code or machine readable executable instructions stored on at least one computer readable medium 102, which when executed, are configured to carry out and execute the processes and methods described herein, including all or part of the embodiments of the present disclosure. The computer readable medium 102 may be a memory of the computing apparatus 100. In alternate aspects, the computer readable program code may be stored in a memory external to, or remote from, the apparatus 100. The memory may include magnetic media, semiconductor media, optical media, or any media which may be readable and executable by a computer. Computing apparatus 100 may also include a processor 104 for executing the computer readable program code stored on the at least one computer readable medium 102. In at least one aspect, computing apparatus may include one or more input or output devices to allow communication among the components of the exemplary imaging system, including, for example, what may be generally referred to as a user interface 106, such as, the operator workstation described above, which may operate the other components included in the imaging system or to provide input or output from the computing apparatus 100 to or from other components of the imaging system.

A general workflow for analyzing a specimen utilizing multiplexing imaging technology, such as, for example, the GE Healthcare MultiOmyx™ platform may include staining the specimen with a particular biomarker and obtaining and storing an image of the stained specimen using, for example, the imaging system disclosed above. The specimen is then bleached of the biomarker or otherwise subjected to a process to inactivate the staining of the biomarker including, for example, chemical inactivation before being stained with a different biomarker after which an image of the specimen stained with the second biomarker is similarly obtained and stored. The sequential staining process may be repeated as described and performed as disclosed in U.S. Pat. No. 7,629,125, which is incorporated by reference herein in its entirety for all purposes.

One embodiment of the present disclosure, in general, determines a staining quality map and score by combining the morphological properties of a segmentation marker and its correlations with two different images: a nuclei marker (for example, DNA counter-stain DAPI) and a background or bleached image from a previous imaging round, the latter image can also referred to as an AF image or auto-fluoresce image. A segmentation quality score may also determined based on the properties of the segmentation image in combination with data obtained in the process of determining the staining quality map and score.

An exemplary workflow for analyzing the quality of a specimen utilizing multiplexing imaging technology, including, for example, the GE Healthcare MultiOmyx™ platform may include staining the specimen with a particular biomarker, such as, for example, a segmentation marker, such as stromal segmentation markers, including, for example, ribosomal protein S6 for cytoplasm, Na+K+ATPase for membrane and epithelial segmentation markers, including, for example, PanCK (pan-cytokeratin). A segmentation marker image of the stained segmentation specimen is obtained and stored using, for example, the imaging system disclosed above. The specimen is then bleached of the biomarker or otherwise subjected to a process to inactivate the staining of the biomarker. An image of the bleached specimen is obtained and stored using the imaging system. The specimen is next stained with a nuclei marker, such as DAPI and a nuclei marker stained image of the specimen is obtained and stored using the imaging system. The nuclei marker stained specimen is then similarly bleached and an image of the post nuclei marker stained specimen is obtained and stored using the imaging system.

Figure 2:
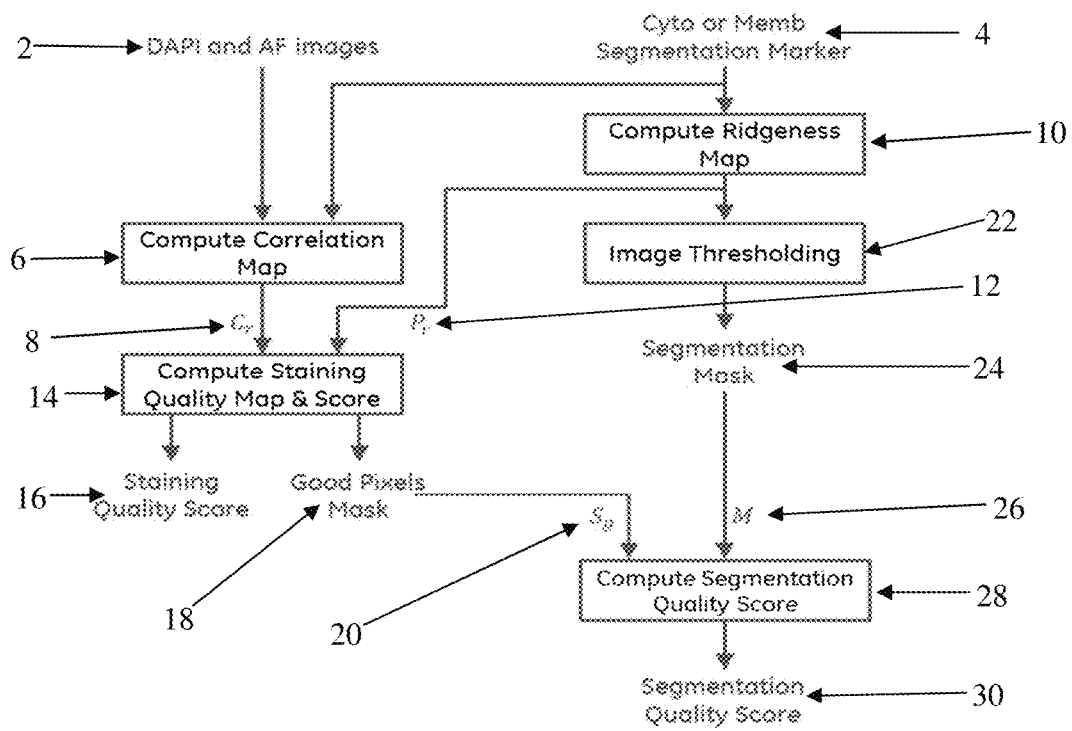
FIG. 2 is a flow diagram illustrating an embodiment of combined staining and segmentation QC workflow for cytoplasm and membrane segmentation markers.
Figure 3:
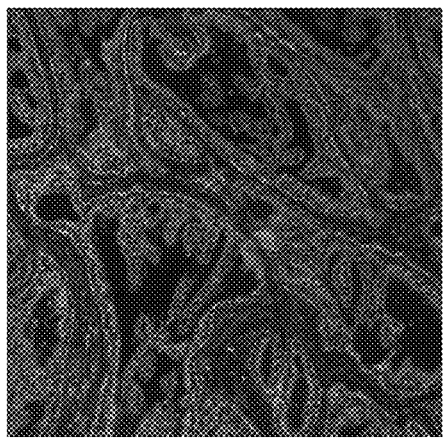
FIG. 3 is a panel of images illustrating outputs from the different steps in FIG. 2 for the S6 image shown in A.
Figure 3:
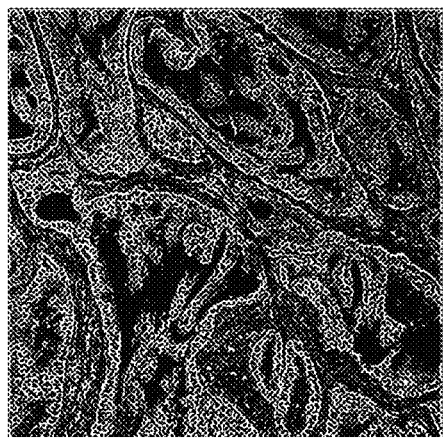
Figure 3:
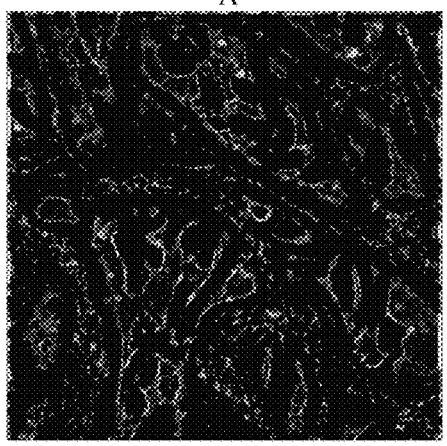
Figure 3:
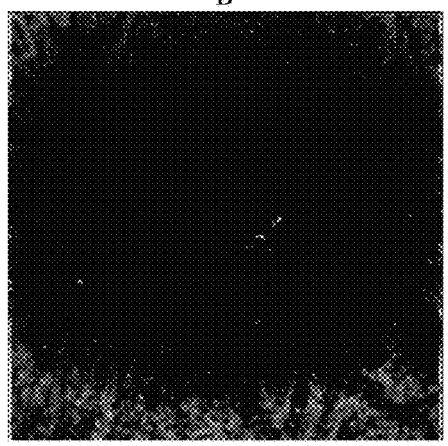
Figure 3:
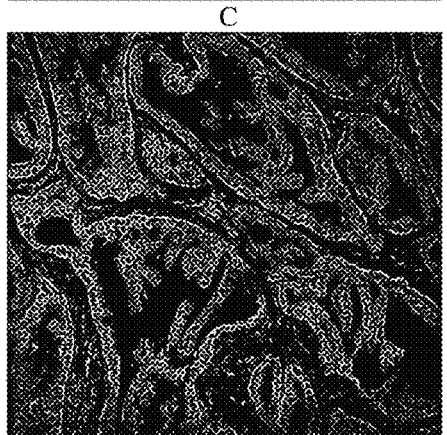
Figure 3:
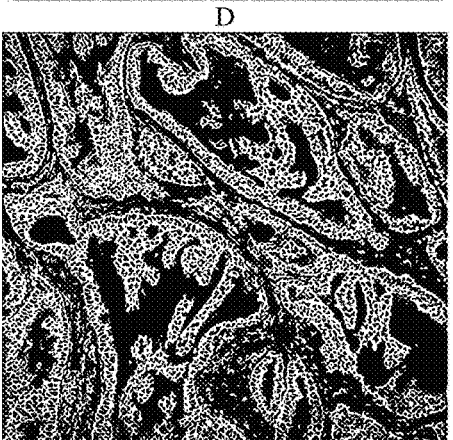

FIG. 2 is a flow diagram of one embodiment of the QC workflow of the present disclosure in which the biomarkers include S6 for cytoplasm or Na+K+ATPase for membrane using, for example, the imaging system previously referenced. Included in 2 of FIG. 2 is a DAPI image obtained and stored of the DNA counter-stain DAPI specimen and the AF (auto-fluorescence) images obtained and stored of the bleached specimen, as described above. The AF image data subsequently utilized may be one or a combination of both bleached specimen images obtained. A segmentation marker for either cytoplasm (for example, S6) or membrane (for example, Na+K+ATPase) is obtained and stored in 4 of FIG. 2, as described above. A sample S6 image is shown in FIG. 3A.

In step 6, a correlation map (Cr) 8 is calculated which represents the probability of each pixel in segmentation marker image to be background or is non-specific. Other terms for a correlation map are a cross-correlation map and a morphology map. (Cr) is scored in the range of 0 to 1 using, for example, normalized cross correlation between the segmentation marker and each of DAPI and AF images, after which, the maximum of the two correlations is taken at each pixel. In the scale of from 0 to 1, 0 indicates that the pixel is less similar and 1 indicates that the pixel is more similar to being background or non-specific with varying degrees of similarity in between. One embodiment includes calculating (Cr) 8 by (1) computing pixel-level cross-correlations, using a sliding window approach, between the segmentation marker image and the corresponding DAPI and bleached/background image (sample correlation maps are shown in FIG. 3C (correlation map with DAPI image and FIG. 3D (correlation map with background image), (2) computing a correlation map by setting the value at each pixel to the maximum of the two correlations (with DAPI and bleached/background images), (3) computing maximum pixel-level projection of the segmentation marker and the bleached/background images and using the corresponding image to compute bright intensity threshold and (4) applying the computed threshold on the bleached/background image to extract bright pixels maps, and use that map to set correlations at non-bright pixels to zero. Computing useable correlation coefficients for the sliding window approach can include, for example, Person's correlation, Rank correlation and distance correlation.

In step 10, a ridgeness probability map (Pr) 12 is determined for the segmentation marker image. Ridgeness measures curvature in an image and the probability that a pixel is part of a tube or ridge based on the surrounding pixels. Ridgeness can indicate whether a pixel is part of a membrane or cytoplasm depending on the segmentation marker used. One embodiment, for example, utilizes Frangi's multi scale vessel enhancement algorithm included in Algorithm (A) below, followed by normalizing the ridgeness values to create a probability map (Pr) in the range of 0 to 1. A sample ridgeness probability map is shown in FIG. 3B.

---

Algorithm A: Steps for computing Frangi's Tubeness (ridgeness) measure ($F_T$) of segmentation markers

---

Let I be an image and $G_\sigma$ be a Gaussian filter where $\sigma$ represents its scale
Let $L_\sigma$ be the Gaussian filtered image (I * $G_\sigma$) at scale $\sigma$
Let H(x, y) be the Hessian matrix at pixel (x, y), which is computed from the second order partial derivatives as follows:

$$H(x, y) = \begin{bmatrix} \frac{\partial^2 L_\sigma(x, y)}{\partial_x^2} & \frac{\partial^2 L_\sigma(x, y)}{\partial_x \partial_y} \\ \frac{\partial^2 L_\sigma(x, y)}{\partial_x \partial_y} & \frac{\partial^2 L_\sigma(x, y)}{\partial_y^2} \end{bmatrix}$$

Let $\lambda_1$ and $\lambda_2$ be the eigenvalues of H such that $|\lambda_1| \geq |\lambda_2|$.
Then, Frangi's tubenss/ridgeness is computed as follows:

$$F_T(x, y) = \begin{cases} (1 - e^{-2R^2})(1 - e^{-8S^2}), & \lambda_1 < 0 \text{ and } \lambda_2 < 0 \\ 0, & \text{otherwise} \end{cases}$$

Where: $R = \frac{|\lambda_1|}{|\lambda_2|}$ and $S = \sqrt{\lambda_1^2 + \lambda_2^2}$

---

Examples of other exemplary means to calculate a ridgeness (tubeness) probability map include the following: Lindeberg, T. (1998). "Edge detection and ridge detection with automatic scale selection". International Journal of Computer Vision 30 (2): 117-154. doi:10.1023/A:1008097225773; Robert M. Haralick (1983). "Ridges and valleys on digital images. Computer Vision". Graphics and Image Processing, 22:28-38, 1983; and Koka, S., Anada, K., Nomaki, K., Sugita, K., Tsuchida, K., Yaku, T (2011). "Ridge Detection with the Steepest Ascent Method". Proc. ICCS 2011, Procedia Computer Science, vol. 4, 2011, pp. 216-221.

Figure 4:
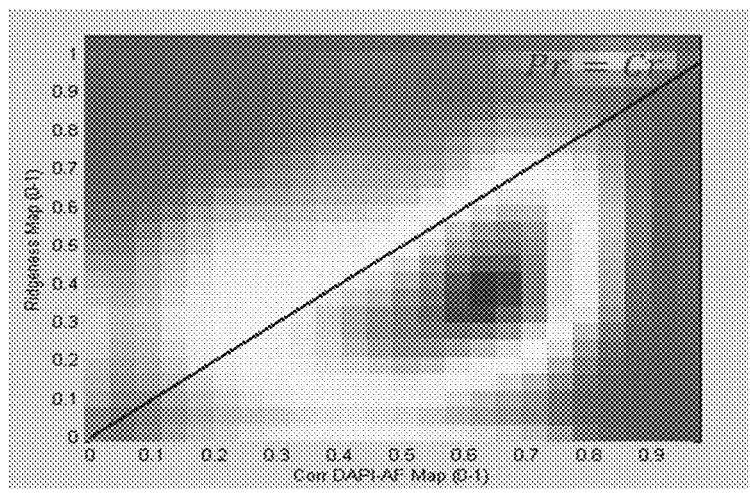
FIG. 4 illustrates an exemplary 2-D histogram of a correlation map (x-axis) and a ridgeness map (y-axis)
Figure 5:
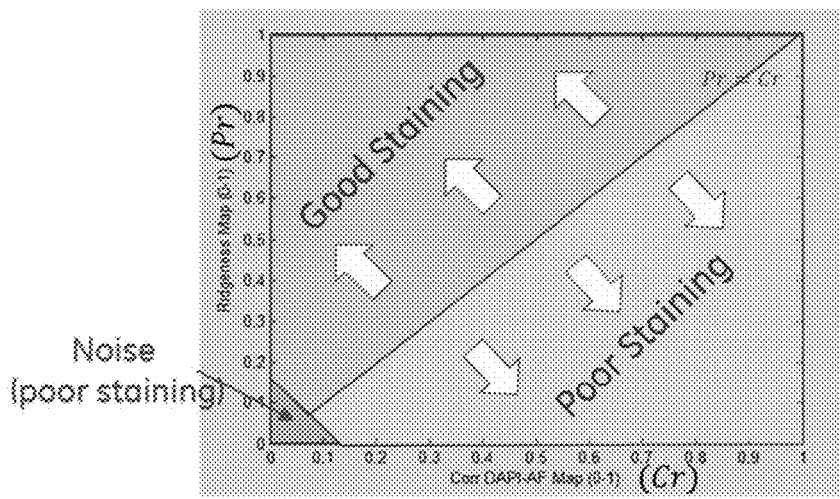
FIG. 5 is an exemplary 2-D histogram illustrating pixels of good and poor staining in terms of ridgeness (Pr) and correlation (Cr) maps.

In step 14, a staining quality map and score are calculated. In one embodiment, a 2-dimensional (2-D) histogram of the ridgeness (Pr) 12 and correlation (Cr) 8 maps as shown, for example in FIG. 4 in which shows the correlation map (Cr) 8 is on the x-axis, the ridgeness map (Pr) 12 is on the y-axis and the identity line (Pr=Cr). The 2-D histogram indicates the number of pixels that have the same ridgeness (Pr) 12 and correlation (Cr) 8 probabilities. In FIG. 4, for example, the darkest red color indicates the where the largest number of pixels fall in the histogram. The ridgeness (Pr) 12 and correlation (Cr) 8 maps are used to extract a set of good quality pixels ($S_g$) as illustrated in FIG. 4 and explained in Algorithm (B) below. In the FIG. 5 example, the good stained pixels are shown above the identity line and the poor stained pixels are shown below the identity line.

Algorithm B: Computing Staining Quality Score $S_q$

Given segmentation marker image I, ridgeness probability map Pr and the correlation map Cr, extract the set of good pixels $S_g$ as follows:
Compute the good staining probability map (Gp). Two methods were implemented:
Method 1: deviation from identity line (Pr(x) = Cr(x)):

$$Gp = \frac{Pr(x) - Cr(x)}{1 + Cr(x)}$$

Method 2: deviation from best-fit line, with zero intercept (Pr(x) = a × Cr(x)):

$$Gp = \frac{Pr(x) - a \times Cr(x)}{1 + a \times Cr(x)}$$

Extract the good staining pixels ($S_g$) as follows:

$$S_g = \{\forall x \in I | Gp > \tau\}$$

Where $\tau$ is the deviation thresholds
Compute staining quality score $S_q$ as follows:

$$S_q = \frac{\|S_g\|}{\|S_b\|} \times 10$$

There are two exemplary embodiments for calculating a good staining probability map (Gp) illustrated in Algorithm B. The first method includes deviation from the identity line (Pr=Cr). The second method includes deviation from the best-fit line (Pr=a×Cr). A sample good staining probability map is shown in FIG. 3E.

The good quality pixels (Sg) are determined from those pixels having a Gp that is greater than $\tau$ where $\tau$ indicates the desired threshold above the identity line. $\tau$ can be selected, for example, by a user or by a system based on desired image and analytical parameters. Once the set of good quality pixels ($S_g$) is determined and labeled as such, the rest of the pixels in the image are labeled and set as bad quality pixels ($S_b$). FIG. 3F shows a sample staining quality map with good quality pixels ($S_g$) colored white and bad quality pixels ($S_b$) colored blue. The staining quality score ($S_q$) 16 can then be calculated as determined in Algorithm (B).

In addition to the staining quality score, a good pixels (staining) mask 18 is determined using the set of good quality pixels ($S_g$) 20 and ($S_g$) 20 can be further utilized to determine a segmentation quality score. Before the segmentation quality score can be determined, in step 22, image thresholding is applied to the ridgeness probability map to extract a segmentation mask 24 (also shown as (M) 26). (M) 26 can also utilized to determine a segmentation quality score. Examples of suitable thresholding methods include Otsu's method, clustering-based thresholding (e.g. k-means), mixture model based thresholding and entropy-based thresholding.

In step 28, the good staining mask 18 (good quality pixels ($S_g$) 20) are used with the segmentation mask 24 ((M) 26) to determine a segmentation quality score 30 as defined in Algorithm (C).

Algorithm C: Computing Membrane and Cytoplasm Segmentation Quality Score

Let $T_p$, $F_p$ and $F_n$ be the sets of true positive, false positive and false negative pixels respectively
Define the segmentation quality score ($Q_S$) as follows:

$$Q_S = 10 \times \frac{\|T_p\|}{\|T_p + F_p + F_n\|}$$

Where $\|\ \|$ represent the cardinality of the set

Figure 6:
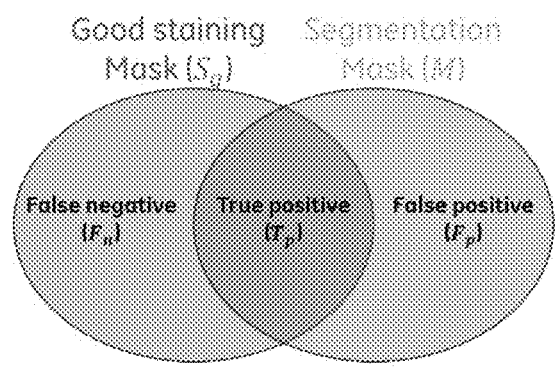
FIG. 6 is a diagram illustrating true positive, false positive and false negative pixels for determining membrane and cytoplasm segmentation quality score.

The true positive, false positive and false negative pixels may be defined as shown in FIG. 6.

Figure 7:
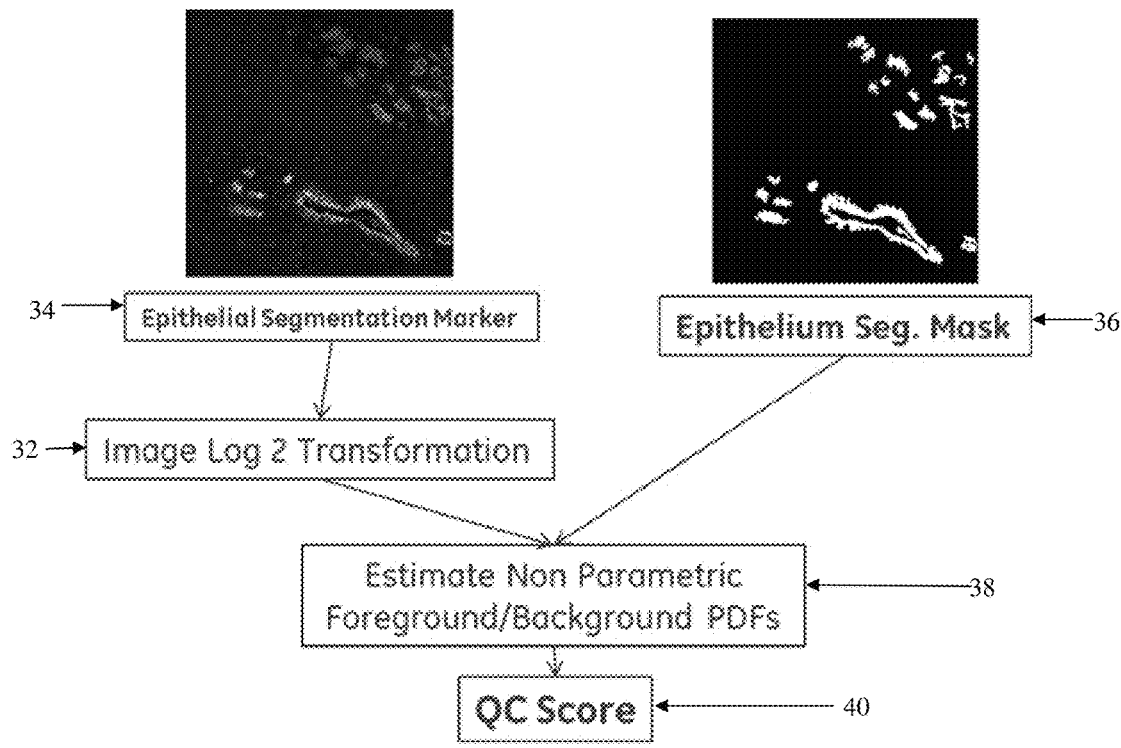
FIG. 7 is a diagram illustrating the epithelial segmentation QC algorithm.

In an embodiment when analyzing specimens are stained with epithelial (epithelium) segmentation markers, the steps illustrated in FIG. 2 can be used to determine the staining quality score 16 as described above. In this embodiment, the segmentation quality score is calculated differently from the method used for cytoplasm and membrane, which is illustrated in the high level diagram shown in FIG. 7. In this process, (1) a Log 2 transform 32 is applied on the epithelial AF image 34, (2) given the Log transformed image and the epithelial segmentation mask 36, in step 38, an estimate of non-parametric probability density functions (PDFs) of the foreground P (x|F) and the background P (x|B) are determined, (3) the segmentation quality score $Q_{ES}$ (QC Score 40) is defined as the probability of overlap between foreground and background PDFs, can be determined as shown in Algorithm (D) below.

Algorithm D: Computing Epithelial Segmentation Quality Score

Let P(x|F) and P(x|B) be the normalized foreground & background PDFs respectively
Define the epithelial segmentation quality score ($Q_{ES}$) as follows:
$Q_{ES} = 10 \times P(x|F \cap B)$

EXAMPLES

Four experiments were performed to evaluate embodiments of the present disclosure utilizing the GE Healthcare MultiOmyx™ platform.

Figure 8:
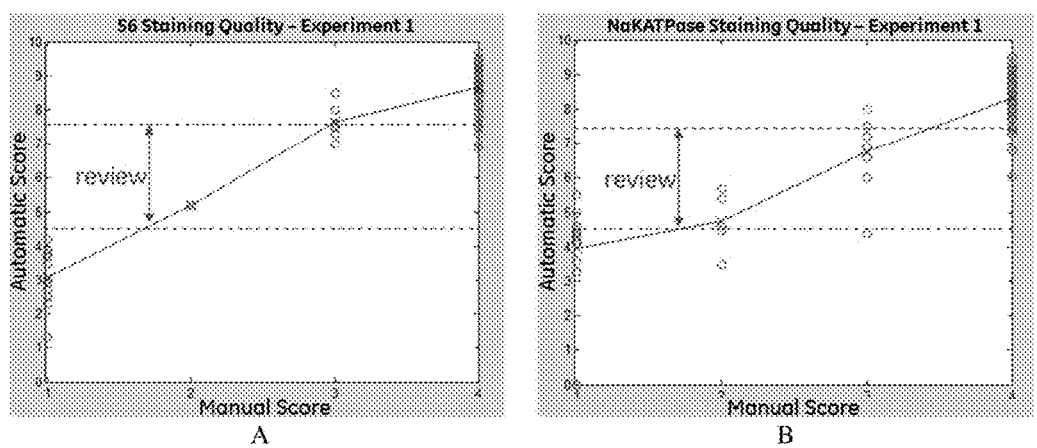
FIG. 8 illustrates manual vs. automated staining QC scores of (A) S6 and (B) NaKATPase from Experiment 1 of the Examples.

In Experiment 1, a staining QC algorithm (Algorithm B) was evaluated for cytoplasm (ribosomal protein S6) and membrane (Na+K+ATPase) segmentation markers using 75 spots (i.e. 150 images) selected from three different studies. First, manual assigning a 0-3 score for each image was performed as explained in table 1. Next, automated staining quality scores were determined and compared to the manual scores. The two plots in FIG. 8 show high agreement between manual and automated scores for both for S6 and NaKATPase with dotted blue lines showing examples of possible acceptance and reject thresholds.

TABLE 1

Definitions of manual staining quality scores used for cytoplasm and membrane segmentation markers

| Manual Staining Quality Score | Definition |
|---|---|
| 1 | 0-25% usable area/pixels |
| 2 | 25-50% usable area/pixels |

TABLE 1-continued

Definitions of manual staining quality scores used
for cytoplasm and membrane segmentation markers

| Manual Staining Quality Score | Definition |
|---|---|
| 3 | 50-75% usable area/pixels |
| 4 | 75-100% usable area/pixels |

Furthermore, an acceptance threshold at 7.5 and a rejection threshold at 4.5 were defined. Images with scores above acceptance threshold were accepted and those below rejection threshold were rejected. Remaining images were marked as "need review". Then, the criteria given in Table 2 were applied.

TABLE 2

Experiment 1 - Evaluation of the automated staining quality scores of the cytoplasm and membrane segmentation markers with respect to manual scores

| Evaluation Criteria | Definitions | Values S6 | NaKATPase |
|---|---|---|---|
| % False Negtive (% FN) | % of image with manual scores 4 or 3 that were rejected | 0% | 1.8% |
| % False Positive (% FP) | % of image with manual scores 1 or 2 that were accepted | 0% | 0% |
| % Possible Errors (% FE) | % of image with manual score 3 that were accepted or images with manual score 2 that were rejected | 5.7% | 3.8% |
| % Speedup (% SP) | % of image with manual scores 4 or 1 that were that were accurately accepted or rejected (respectively) | 94% | 83% |

Figure 9:
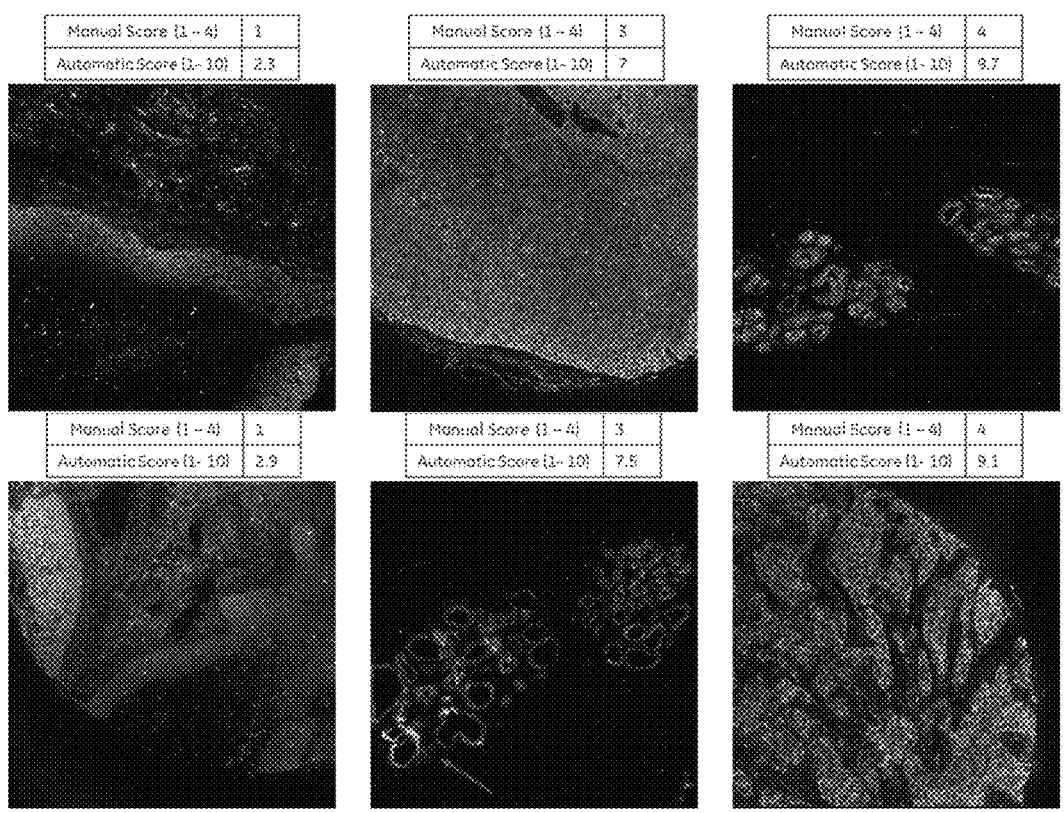
FIG. 9 is a panel of sample S6 images and their manual and automated quality scores from Experiment 1 of the Examples.
Figure 10:
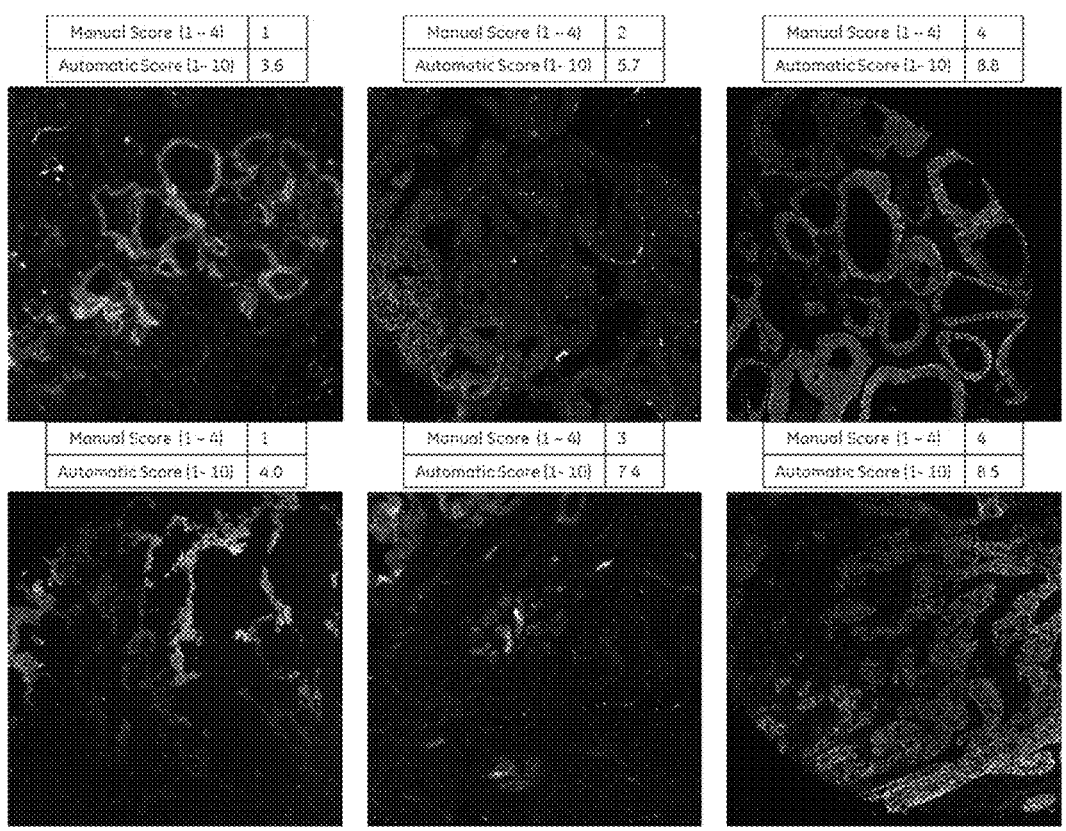
FIG. 10 is a panel of sample NaKATPase images and their manual and automated quality scores from Experiment 1 of the Examples.

The algorithm significantly reduced the number of good (score 4) or poor (score 1) images that need manual review and resulted in very low false positive and false negative rates. FIGS. 9 and 10 respectively show sample S6 and NaKATPase images with their scores. In FIG. 9, the red arrow in the two middle images show areas with poor staining that resulted in lower scores than expected.

Figure 11:
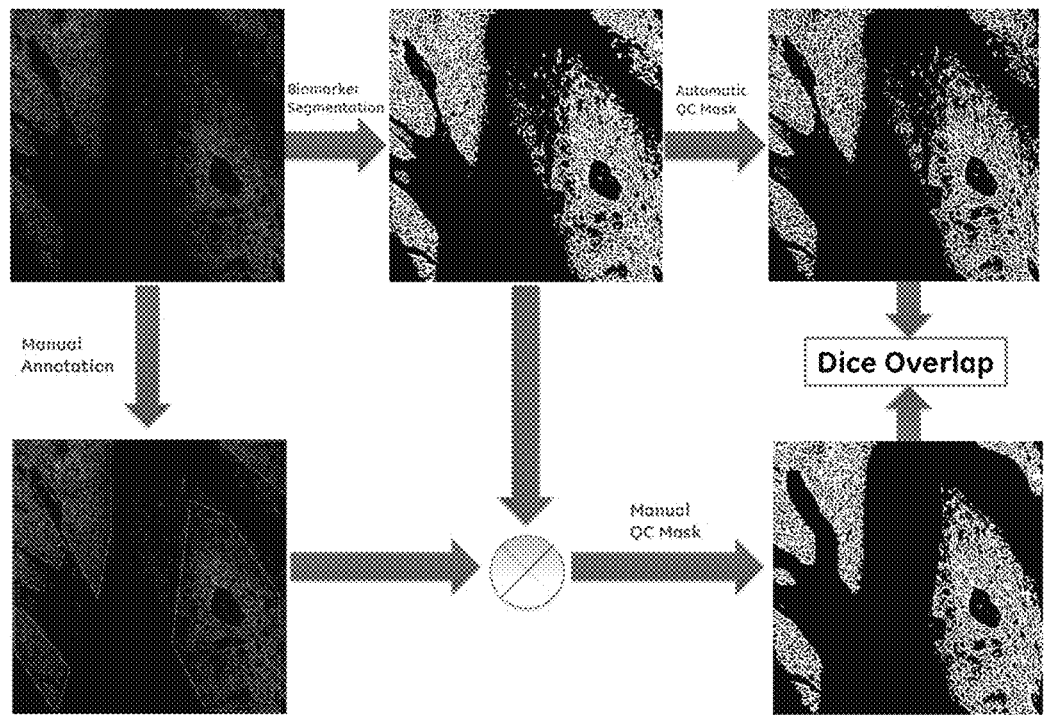
FIG. 11 is a flow diagram illustrating the steps of Experiment 2 of the Examples for evaluating the staining QC algorithms of the cytoplasm and membrane segmentation markers.
Figure 12:
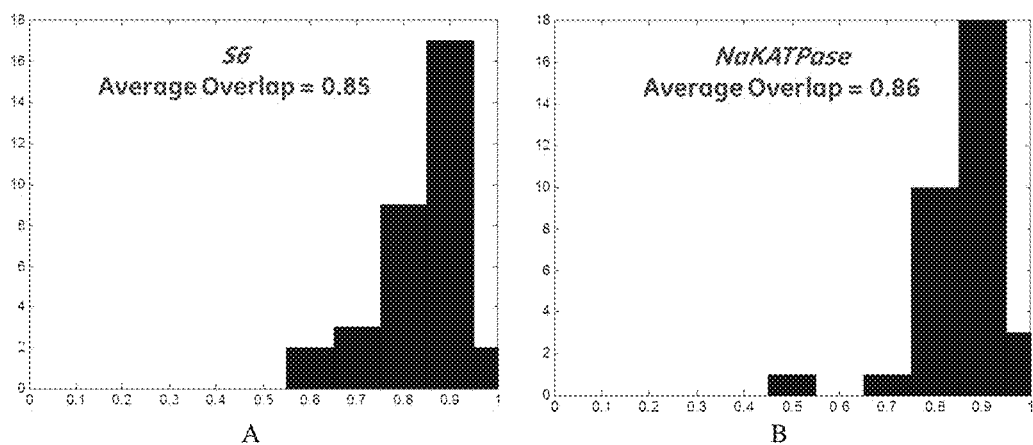
FIG. 12 illustrates manual vs. automated staining QC masks (good staining masks) of (A) S6 and (B) NaKATPase from Experiment 2 of the Examples.
Figure 13:
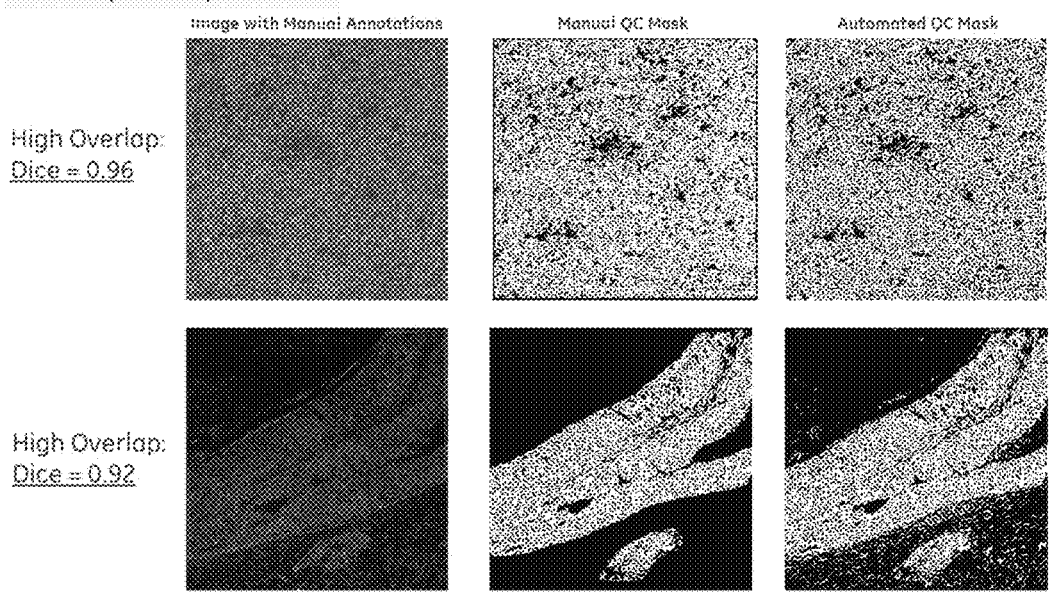
FIG. 13 is a panel of sample S6 images with their manual and automated QC mask and the corresponding overlap from Experiment 2 of the Examples.
Figure 14:
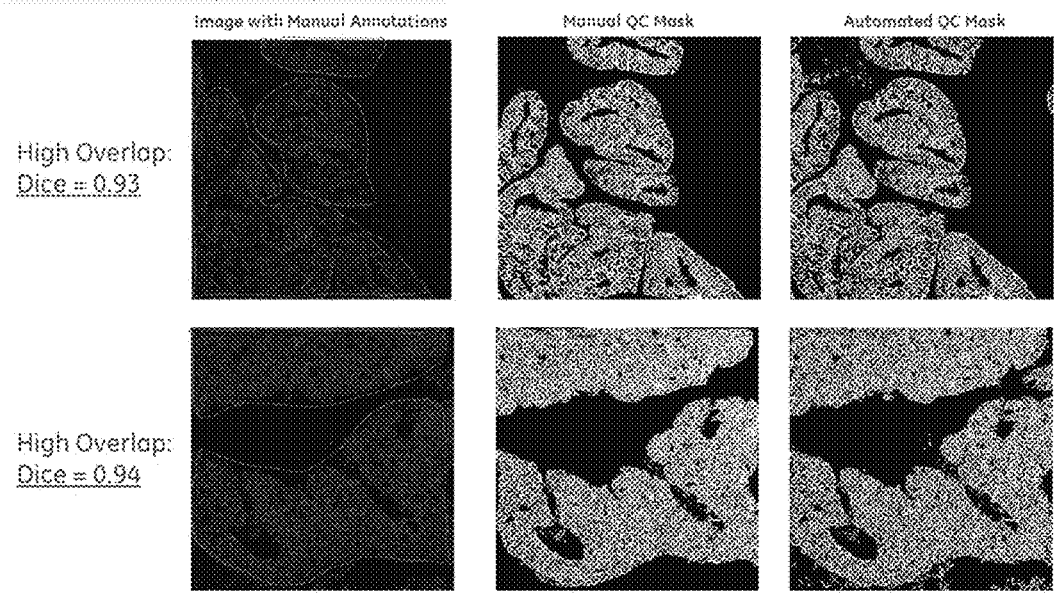
FIG. 14 illustrates a panel of sample NaKATPase images with their manual and automated QC mask and the corresponding overlap from Experiment 2 of the Examples.

In Experiment 2, 33 spots were selected for both cytoplasm (S6) and membrane (NaKATPase) segmentation markers (i.e. 66 images). Then, scores were determined using the approach illustrated in FIG. 11 for evaluating the staining QC algorithms of the cytoplasm and membrane segmentation markers. First, a pathologist annotated/marked good regions in each image. Second, image segmentation was performed to extract a marker mask and extracted good quality pixels within that mask using Algorithm B. That resulted with an automatic QC mask. Simultaneously, a manual QC mask was extracted as the intersection of manual annotations with the marker mask. Finally, a Dice overlap score (range: 0-1) was computed between the automatic and manual QC masks and used that as a measure of agreement. Dice overlap distributions for all of the images are shown in FIG. 12 in which distributions of Dice overlap scores of (A) S6 and (B) NaKATPase show overlap/agreement. Clearly, the algorithm resulted with high overlap between manual and automatic QC masks (average overlap=0.85). FIG. 13 shows some results of sample S6 images with their manual and automated QC mask and the corresponding overlap and FIG. 14 show some results of sample NaKATPase images with their manual and automated QC mask and the corresponding overlap.

In Experiment 3, cytoplasm and membrane segmentation qualities were evaluated using 39 spots (i.e. 78 images) using Algorithm C. In doing so, each segmentation marker image was segmented and then a 0-2 manual score (defined in table 3) was assigned to each segmentation mask.

TABLE 3

Definitions of manual segmentation quality scores used
for cytoplasm and membrane segmentation markers

| Manual Segmentation Quality Score | Definition |
|---|---|
| 0 | Poor segmentation, with more than 50% bad mask area |
| 1 | OK segmentation, with more than 25% bad mask area, but less than 50% |
| 2 | Good segmentation, with less than 25% bad mask area |

Figure 15A:
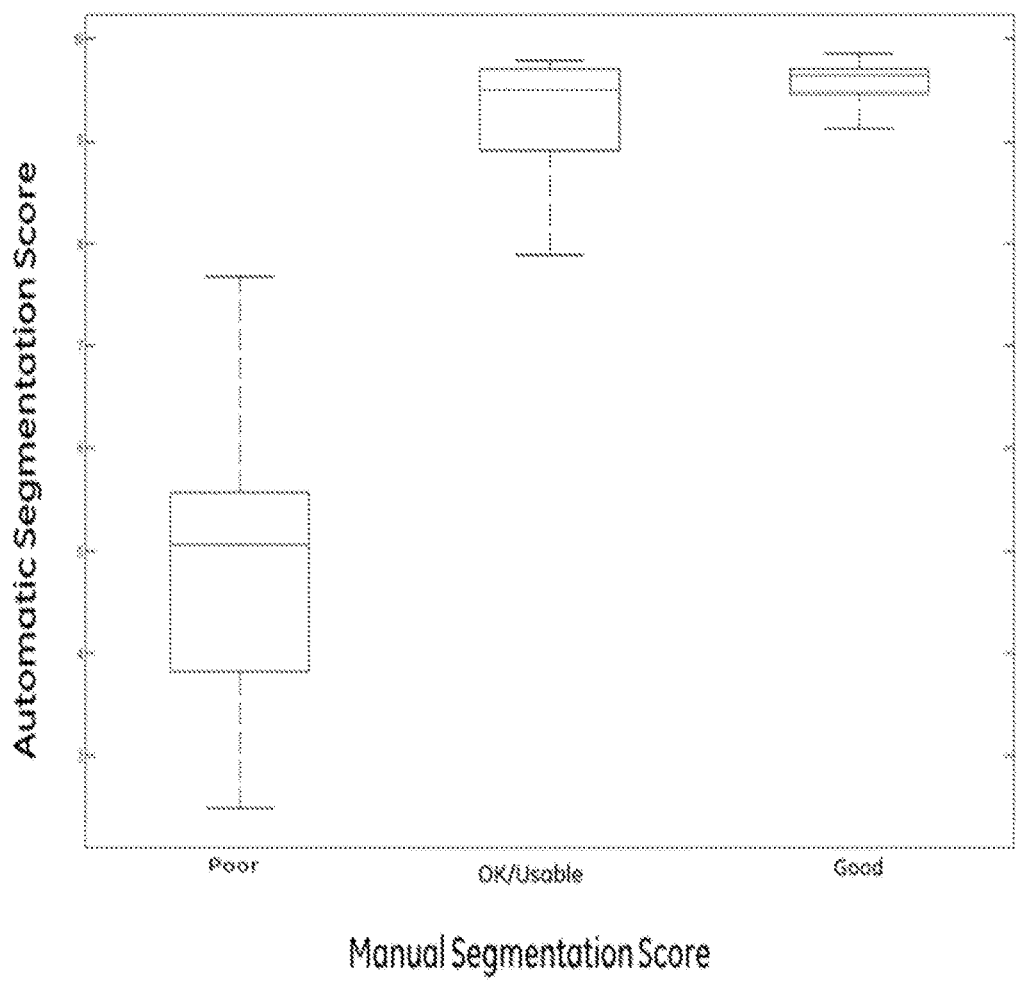
FIG. 15A and 15B illustrate manual vs. automated segmentation QC scores of S6, and NaKATPase from Experiment 3 of the Examples, respectively.
Figure 15B:
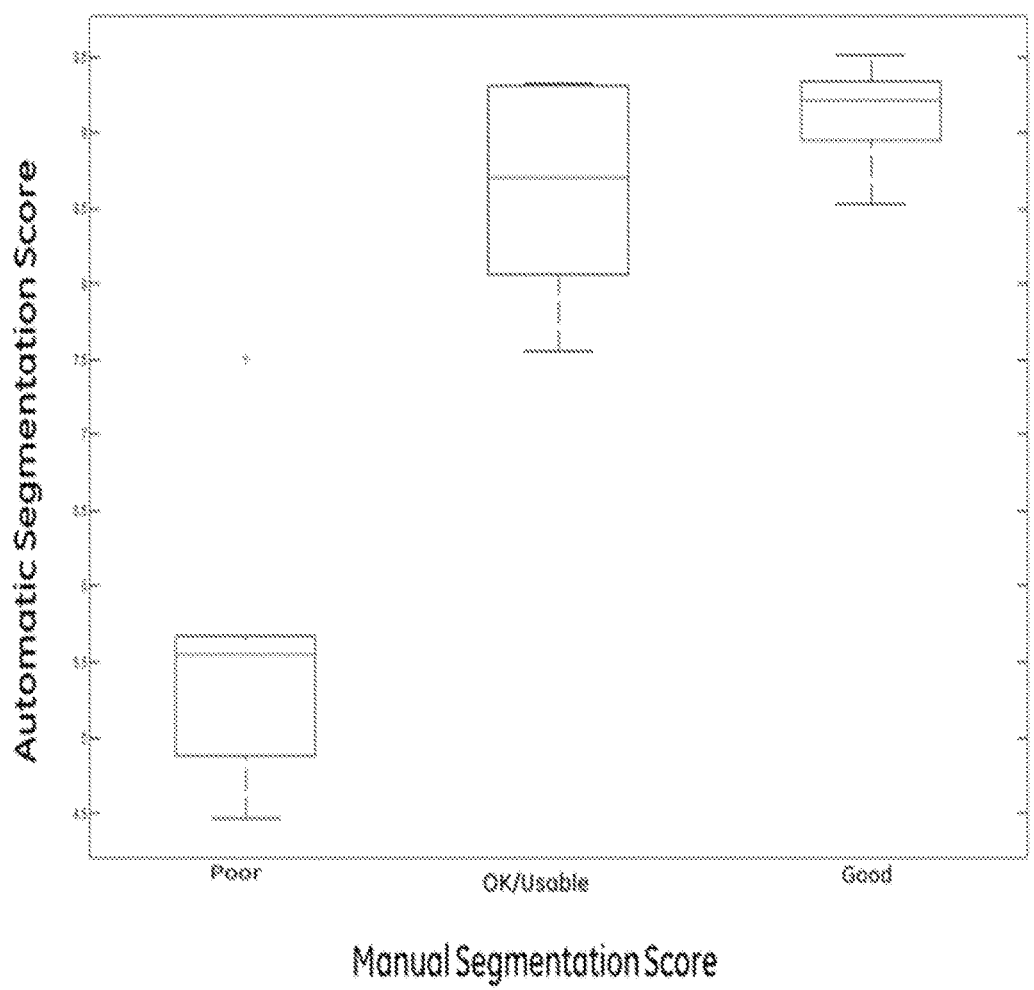

Next, automated segmentation quality scores were determined using Algorithm C and compared to manual scores. As a result, very good agreement between the manual and automated scores was found, especially in separating poor quality cases from OK and good cases as illustrated in FIG. 15A that shows manual vs. automated segmentation QC scores of S6 and FIG. 15B that shows manual vs. automated segmentation QC scores of NaKATPase.

Figure 16:
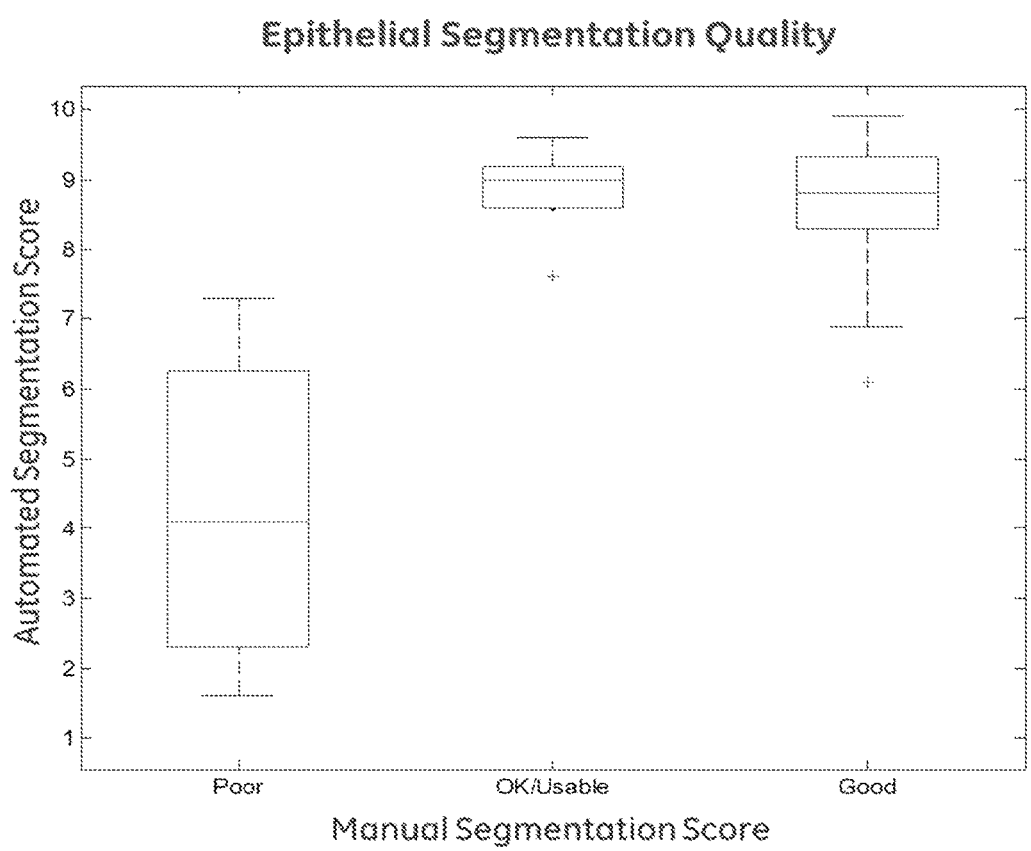
FIG. 16 illustrates manual vs. automated segmentation QC scores of epithelial segmentation from Experiment 4 of the Examples.

In Experiment 4, the same 39 spots in Experiment 3 were used to evaluate the epithelial segmentation quality scores. First, manual quality scores were determined following the same criteria used in the previous experiment (Table 3). Next, the automated scores were computed using Algorithm D and compared to the manual scores. As shown in the in FIG. 16 that shows manual vs. automated segmentation QC scores of Epithelial Segmentation, the algorithm performed well especially in separating poor segmentation cases from OK and good segmentation cases.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining the quality of a segmentation marker stained biological specimen, comprising:
   Acquiring separate image data of an unstained form of a biological specimen, the biological specimen stained with a nuclei marker and the biological specimen stained with a segmentation marker;
   Determining a correlation map (Cr) from the separate image data of the unstained form of the biological specimen, the biological specimen stained with the nuclei marker and the biological specimen stained with a segmentation marker;

Determining a ridgeness map (Pr) from the image data of the biological specimen stained with the segmentation marker; and Determining a staining quality score from the correlation map (Cr) and the ridgeness map (Pr), wherein the step of determining the staining quality score comprises:

i. Determining good staining probability map (Gp) by one of two methods:

Method 1: deviation from identity line (Pr(x)=Cr(x)):

$$Gp = \frac{Pr(x) - Cr(x)}{1 + Cr(x)}$$

Method 2: deviation from best-fit line, with zero intercept (Pr(x)=a×Cr(x):

$$Gp = \frac{Pr(x) - a \times Cr(x)}{1 + a \times Cr(x)}$$

ii. Extracting good staining pixels ($S_g$) as follows:

$$S_g = \{\forall x \in I | Gp > \tau\}$$

where τ is a deviation threshold; and iii. Computing a staining quality score $S_q$ as follows:

$$S_q = \frac{\|S_g\|}{\|S_b\|} \times 10$$

wherein $S_b$ represents the rest of pixels in an image once the good quality pixels (Sg) are extracted from the image.

2. The method of claim 1, wherein the nuclei marker is DAPI.

3. The method of claim 1, wherein the segmentation marker is a cytoplasm segmentation marker, a membrane segmentation marker or an epithelium segmentation marker.

4. The method of claim 3, wherein the cytoplasm segmentation marker is ribosomal protein S6.

5. The method of claim 3, wherein membrane segmentation marker is Na+K+ATPase.

6. The method of claim 3, wherein epithelium segmentation marker is PanCK.

7. The method of claim 3, wherein the segmentation marker is the cytoplasm segmentation marker or the membrane segmentation marker, further including determining a segmentation quality score (Qs) comprising:

Extracting good staining pixels ($S_g$) from the correlation map (Cr) and the ridgeness map (Pr);

Extracting a segmentation mask (M) by applying thresholding to the ridgeness map (Pr); and Determining the segmentation quality score ($Q_s$) from the good staining pixels ($S_g$) and the segmentation mask (M).

8. The method of claim 7, wherein the segmentation marker is the cytoplasm segmentation marker or the membrane segmentation marker, further including determining a segmentation quality score ($Q_s$), the method further comprising:

Determining the segmentation quality score ($Q_s$) as follows $$Q_S = 10 \times \frac{\|T_p\|}{\|T_p + F_p + F_n\|}$$

Where ∥ ∥ represents the cardinality of the set, $T_p$ are pixels that are common to ($S_g$) and (M), $F_p$ are pixels in (M) and not ($S_g$) and $F_n$ are pixels in ($S_g$) and not (M).

9. The method of claim 3, wherein the segmentation marker is the epithelium segmentation marker, further including determining an epithelium segmentation quality score ($Q_{ES}$) comprising:

i. Applying a Log 2 transform on an epithelium segmentation marker image;

ii. Estimating the non-parametric probability density functions (PDFs) of the normalized foreground P(x|F) and background P(x|B); and iii. Determining the epithelium segmentation quality score ($Q_{ES}$) as follows:

$$Q_{ES} = 10 \times P(x|F \cap B).$$

10. The method of claim 1, wherein the acquired image of the unstained form of the biological specimen is a background image.

11. The method of claim 1, wherein the step of acquiring the separate image data includes sequentially staining and bleaching the biological specimen with the nuclei marker and the segmentation marker.

12. The method of claim 1, wherein the step of acquiring the separate image data includes:

i. Staining the biological specimen with the segmentation marker to form a segmentation marker stained biological specimen;

ii. Acquiring an image of the segmentation marker stained biological specimen;

iii. Bleaching the segmentation marker stained biological specimen to form a first bleached biological specimen;

iv. Acquiring an image of the first bleached biological specimen;

v. Staining the first bleached biological specimen with the nuclei marker to form a nuclei marker stained biological specimen;

vi. Acquiring an image of the nuclei marker stained biological specimen;

vii. Bleaching the nuclei marker stained biological specimen to form a second bleached biological specimen; and viii. Acquiring an image of the second bleached biological specimen.

13. The method of claim 12, wherein the step of acquiring image data of the unstained form of the biological specimen includes at least one of acquiring the image of the first bleached biological specimen and acquiring the image of the second bleached biological specimen.

14. The method of claim 1, wherein the step of determining the ridgeness map (Pr) includes determining the Frangi's Tubeness (ridgeness) ($F_T$).

15. The method of claim 14, wherein determining the Frangi's Tubeness (ridgeness) ($F_T$) comprises:

$$F_T(x, y) = \begin{cases} (1 - e^{-2R^2})(1 - e^{-8S^2}), & \lambda_1 < 0 \text{ and } \lambda_2 < 0 \\ 0, & \text{otherwise} \end{cases}$$

Where:

$$R = \frac{|\lambda_1|}{|\lambda_2|} \text{ and } S = \sqrt{\lambda_1^2 + \lambda_2^2}$$

in which I is an image, $G_\sigma$ is a Gaussian filter where σ represents its scale, $L_\sigma$ is the Gaussian filtered image ($I*G_\sigma$) at scale σ, H(x,y) is the Hessian matrix at pixel (x,y), computed from the second order partial derivatives as follows:

$$H(x, y) = \begin{bmatrix} \frac{\partial^2 L_\sigma(x, y)}{\partial_x^2} & \frac{\partial^2 L_\sigma(x, y)}{\partial_x \partial_y} \\ \frac{\partial^2 L_\sigma(x, y)}{\partial_x \partial_y} & \frac{\partial^2 L_\sigma(x, y)}{\partial_y^2} \end{bmatrix}$$

and $\lambda_1$ and $\lambda_2$ are the eigenvalues of H such that $|\lambda_1| \geq |\lambda_2|$.

16. A system for assessing the quality of a segmentation marker stained biological specimen, comprising:

A memory configured to store instructions for:
  Acquiring separate image data of an unstained form of a biological specimen, the biological specimen stained with a nuclei marker and the biological specimen stained with a segmentation marker;
  Determining a correlation map (Cr) from the separate image data of the unstained form of the biological specimen, the biological specimen stained with the nuclei marker and the biological specimen stained with the segmentation marker;
  Determining a ridgeness map (Pr) from the image data of the biological specimen stained with the segmentation marker; and
  Determining a staining quality score from the correlation map (Cr) and the ridgeness map (Pr); and A processor configured to execute the instructions stored in the memory, wherein the step of determining the staining quality score comprises:

i. Determining good staining probability map (Gp) by one of two methods:
  Method 1: deviation from identity line (Pr(x)=Cr(x):

$$Gp = \frac{Pr(x) - Cr(x)}{1 + Cr(x)}$$

Method 2: deviation from best-fit line, with zero intercept Pr(x)=a×Cr(x)):

$$Gp = \frac{Pr(x) - a \times Cr(x)}{1 + a \times Cr(x)}$$

ii. Extracting good staining pixels ($S_g$) as follows:

$S_g = \{\forall x \in I | Gp > \tau\}$ where τ is a deviation threshold; and iii. Computing a staining quality score $S_q$ as follows:

$$S_q = \frac{\|S_g\|}{\|S_b\|} \times 10$$

wherein $S_b$ represents the rest of pixels in an image once the good quality pixels (Sg) are extracted from the image.

17. An imaging system for assessing the quality of a segmentation marker stained biological specimen, comprising:

An imager configured to acquire image data of a biological specimen;
Data processing circuitry configured to process the image data into processed image data;
A memory configured to store:
  The image data;
  The processed image data; and
  Instructions for:
    Acquiring separate image data of an unstained form of the biological specimen, the biological specimen stained with a nuclei marker and the biological specimen stained with a segmentation marker;
    Determining a correlation map (Cr) from the separate image data of the unstained form of the biological specimen, the biological specimen stained with the nuclei marker and the biological specimen stained with the segmentation marker;
    Determining a ridgeness map (Pr) from the image data of the biological specimen stained with the segmentation marker; and
    Determining a staining quality score from the correlation map (Cr) and the ridgeness map (Pr),
wherein the data processing circuitry is configured to execute the instructions stored in the memory, and
wherein the step of determining the staining quality score comprises:

i. Determining good staining probability map (Gp) by one of two methods:
  Method 1: deviation from identity line (Pr(x)=Cr(x)):

$$Gp = \frac{Pr(x) - Cr(x)}{1 + Cr(x)}$$

Method 2: deviation from best-fit line, with zero intercept (Pr(x)=a×Cr(x)):

$$Gp = \frac{Pr(x) - a \times Cr(x)}{1 + a \times Cr(x)}$$

ii. Extracting good staining pixels ($S_g$) as follows:

$S_g = \{\forall x \in I | Gp > \tau\}$ where τ is a deviation threshold; and iii. Computing a staining quality score $S_q$ as follows:

$$S_q = \frac{\|S_g\|}{\|S_b\|} \times 10$$

wherein $S_b$ represents the rest of pixels in an image once the good quality pixels (Sg) are extracted from the image.

18. The system of claim 17, comprising
System control circuitry configured to operate and control the imager, data processing circuit and memory; and
A workstation configured to interface with the system control circuitry in order to display image data and processed image data; control the imager, data processing circuit and memory; and implement and control the instructions stored in the memory.

19. The system of claim 18, wherein the imager, data processing circuitry, memory, system control circuitry and workstation are each connected through wires, lines, wireless interfaces, network or communication interfaces including local and wide area intranets, storage networks and the Internet.

* * * * *